(12) United States Patent
Howard et al.

(10) Patent No.: US 8,115,060 B2
(45) Date of Patent: Feb. 14, 2012

(54) MEANS AND METHODS OF CONTROLLING PLANT SEED GERMINATION

(75) Inventors: John Howard, Cayucos, CA (US); Erin Engelkrout, San Luis Obispo, CA (US)

(73) Assignee: Applied Biotechnology Institute, Inc., San Luis Obispo, CA (US)

( * ) Notice: Subject to any disclaimer, the term of this patent is extended or adjusted under 35 U.S.C. 154(b) by 283 days.

(21) Appl. No.: 12/390,485

(22) Filed: Feb. 22, 2009

(65) Prior Publication Data

US 2009/0217418 A1 Aug. 27, 2009

Related U.S. Application Data

(60) Provisional application No. 61/030,573, filed on Feb. 22, 2008.

(51) Int. Cl.
*C12N 15/82* (2006.01)
*C12N 15/29* (2006.01)
*C12N 15/63* (2006.01)
*C12N 15/09* (2006.01)
*A01H 5/10* (2006.01)

(52) U.S. Cl. ..... 800/290; 800/287; 800/295; 435/320.1; 435/468; 536/23.1; 536/23.7; 536/23.5

(58) Field of Classification Search .......... None
See application file for complete search history.

(56) References Cited

U.S. PATENT DOCUMENTS

| | | | |
|---|---|---|---|
| 5,767,379 A * | 6/1998 | Baszczynski et al. ..... | 800/320.1 |
| 5,962,769 A | 10/1999 | Albertson et al. | |
| 7,449,317 B2 | 11/2008 | Bower et al. | |
| 7,750,207 B2 * | 7/2010 | Wu et al. ..................... | 800/287 |

OTHER PUBLICATIONS

Argarana, Carlos E., et al, "Molecular cloning and nucleotide sequence of the streptavidin gene", Nucleic Acids Research, vol. 14, No. 4, 1986, pp. 1871-1882.

Chen, Feng, et al., "Two Tomato Expansin Genes Show Divergent Expression and Localization in Embryos during Seed Development and Germination", Plant Physiology, Nov. 2001, vol. 127, pp. 928-936.

Domoto, Chieko, et al., "Isolation and characterization of two distinct cDNA clones encoding corn seed cysteine proteinases", Elsevier—Biochimica et Biophysica Acta 1263 (1995) pp. 241-244.

Guo, Ze-Jian, et al., "Effect of Intracellular Glutathione Level on the Production of 6-Methoxymellein in Cultured Carrot (*Daucus carota*) Cells", Plant Physiol. (1993), vol. 102, pp. 45-51.

Hood, Elizabeth E., et al., "Commercial production of avidin from transgenic maize: characterization of transformant, production, processing, extraction and purification", Kluwer Academic Publishers—Molecular Breeding (1997), vol. 3, pp. 291-306.

Jensen, Lisbeth Gath, et al., "Transgenic barley expressing a protein-engineered, thermostable (1,3-1,4)-β-glucanase during germination", Proc. Natl. Acad. Sci. USA—Applied Biological Sciences, vol. 93, pp. 3487-3491, Apr. 1996.

Khursheed Bushra, et al., "Quantitive Comparison of Steady-State mRNA Levels From Individual Members of the Two Different Families Expressed in Aleurone Cells", The Journal of Biological Chemistry, vol. 263, No. 35, pp. 18953-18960, Dec. 15, 1988.

Maugenest, Sebastien, et al., "Cloning and characterization of a cDNA encoding a maize seedling phytase", Biochem. J. (1997) vol. 322, pp. 511-517.

Maugenest, Sebastien, et al., "Structure of two maize phytase genes and their spatio-temporal expression during seedling development", Plant Molecular Biology, vol. 39, pp. 503-514, 1999.

Nuutila, A.M., et al., "Expression of fungal thermotolerant endo-1,4-β-glucanase in transgenic barley seeds during germination", Plant Molecular Biology, vol. 41, pp. 777-783, 1999.

Slakeski, Nada, et al., "Development Regulation of (1-3,1-4)-β-Glucanase Gene Expression in Barley", Plant Physiol. (1992) vol. 99, pp. 1226-1231.

Young, Todd E., et al., "Cloning of an α-Amylase cDNA from Aleurone Tissue of Germinating Maize Seed", Plant Physiol. (1994) vol. 105, pp. 759-760.

* cited by examiner

*Primary Examiner* — Brent T Page
(74) *Attorney, Agent, or Firm* — McKee, Voorhees & Sease, P.L.C.

(57) ABSTRACT

A method of controlling germination of seed is provided in which a nucleic acid encoding a protein which causes inhibition of germination is transformed into a plant, operably linked with a promoter that expresses during germination. The protein is one in which a restoring substance can be applied to the seed and restores germination. Also provided is an amylase germination preferred promoter.

17 Claims, 7 Drawing Sheets

```
TGTCAAGCTTTCAACGCACATGTTTTATGATGTATTTTTAAATGGTCGATACCAACAATTGATACATCAG
TAAGTTGAGCATTACAGAAATGCCAATAGGTGGCATACCTTATCTTCTCACGATTGACGTCTTTGAACAA
CCATTCGAAGTCGTTTCGTACATCATGGGTGCTCTTGCAACCCTTCTTGTGGCAAACAGTGTTGGTGGCT
CGCGTGACTGTGGCTTAGCTTCCCAAGACATCATCAGCATTGGTGGGACTTGGGGATCTACAAATGAATA
ACCCACGTTGTCATCTCAGGGATATCAGTCCATGGATGACAAGACGTTGTCACACGTCGCACAACCACAT
GAAGTCTTTGAGACGGGCAACATGGAGGACGGGCAAGGCCGCGTCGATGTGAAGGACGGACGAGGTTAGA
GAGGACGAGCGCAACCAAGGAAGATAGCATAGGCCACGTCAGTGGCGGATCCAGAAACAGATCATGAGGG
GGCTACGAAACTAAAGCTATAAAATTCTTTTAAAAAACAATCTAATTGATGTTAATATAACACAATTAGC
AAGATAAAACTTAAATACTCAAAAGGCATGTAGCCTAAATAAGTCGGCACGAATTCTACAAATATAATAA
TAAATAATCAATACATATCGTTCTGATTCTTGATAAGGAATATATCCATCCTATCCCTATAAACATAAAA
TTTAATTTTATCAACTAACCTACTAACCTAGCAGATAATTGATTAAACCAAAATACCAAATAATCTCACC
TTCTTATTTAGCACAGTAGCTCTAGCAGCCCCAGGCACATAGCAAACTAGCAGCAGAAGCAGTGCAACCG
GATTCATTGGTTCACTTTTCATCAATCAGCAGGGACAAGGAGGCTTCACGAGGTGTATAGCATGCTCACA
CATGACGCCTCCACACTCCACTTCACGGAGCAGCCAACAAGCACCGAGCAGGCGAGCAGCCAGTGGGGGA
GGCGACACCTGATTGAGTCCTGATCCCTGATGGAGTGAGGGAGCGGGACTGAGGACAGCGGCCGGTGTGG
GGGAGGACAGGAGGAGCCGAGGGCGCAGGCTACACTGCCGATGTGCCGCAACGCGTGCGGGAGGAGCCAT
GGGCGCAGCGCGGACGTGCAGTGCGGAGGGATGAAGAGCGGCCAGCAGCGGCTGGGCGCGTGTGAAGAGG
TGATGTGAGAATCTGACCTAGCTTTTTAGATTTTTATGGGTCAAATTTACTATATATCAATGTTTCTAAT
GGACCACGATCGGGGCTGCAGCCTGGACAGCCCCGATCGCACATCCACCCCTGGCCCAGGTCATAATTGT
CAGCCAGAAAGAAGATACATAAAAGAGATGACAAATATATCTCACATACCATTTTTTTAATAAGATTAAA
TAGCAAGGGATTTTCTCTACATAGATCTCTTCTATTTTCTTTGTTACCAAATCAGCTTTGAAGGTGCACC
AACGGAAAATCTGTTCGCCGCGTCCATGACTCCCAGTCCCTGGTCCCTGCACGTCTGCACTGTACCGGCA
ACCCCATCCCCATGCACAACACGGCTCAGACCCCACGTACCTTTTTATCCCCCTCTTTAATGTGCCACGA
TAGCATTACACTTTCCGCCATCATCCATATGTCGTCGCTCTCGTTAGAAGCAACGGAGCTTATCCATCGT
TAGTCCGTTACAACGATCCGCCGGCGCCAAACGACCGCCGGATCCAATATAAATACCCTTGCACAGGCAT
GGTGATCGACACACAGCCAAAGTACAAGACTCACTTGCATTTTTGGCACACCAGCACAGAAGAAGAAAAA
AAAAACAGGCACTGAGCTGAGATG
```

Figure 7

1 aagcttaaag atcccattgg aagttaaact ctcggaaaga gttgatcgga tgttagacta
61 acttctgacg gtcgttgggg cccatcggaa gttagcgacg tagacgttgt tagcaccgaa
121 acttctaacc attttagtgg cctctcggaa gttattgtgc taacttccaa ggggtcccac
181 cggcttctca aaagttaatg tgctaacttc aggccatttt agtggcctct cgaaatttat
241 attgaaccaa cattcaaaat gttatttatt ttcaaatttc actatatttc aatacatcgg
301 gatacaaaca atcaggataa caacactaac tgcaatagca tctcatctgt ttcatcacaa
361 taacaccaca cctcataaat ctcatcaatt aaacacaatt ccaatatatt tcttcaaaat
421 aagaactcaa ttagtctcat ctcaacccaa gacacatccc aaatgtctta cagggttcac
481 aagttcacct cccatctatt tgaactatat cttatatatt aacaaacaac attagtttaa
541 atatcataca tttagttatg tctctttcct cattttact cgtagccatg attttgttt
601 agttttgcct cttctgctct tcagcaacag aataacaaaa ctgagtagaa aatacaacta
661 agggtaaaaa taaggaaagc ggtagaacta acggcaccac ttcaaaatgt cgtagtttaa
721 ataatttgat gttcatcaaa tactaaaatt caaaattaaa gacctctaga gtatattttt
781 cttacaagct ccagtggtgg ccgtgcctcg cgtggccata atcatcctta gtatgattga
841 tcatggacag ggtacagacc catgcttgac ttgataaaac accaacaata ccagacccca
901 tccccttccc tatcaacaac ggagggacga tgatatatta tttaggtctt gttcggatac
961 tctactatta tattcactct aaatcatatg tgttaatact agagtaccta aacaaggtct
1021 taagtgcatg cacgtgctgc acgctgttat ggacctatta ggtagtagta ggtcgagtag
1081 gatatatatc acaaagttgt atacctataa atagctcgct ttgataacat gatctgctgc
1141 cttatacgaa acatagctac ctactactca agtatccatc cttattgtaa *gtgctcttat*
1201 *aagctactac tagttacaag ctggtttata tttaactaca agtagcaacg atttgtctta*
1261 *gtatatatgg ttcataatac atatatattg gaactgagat aatatatgca* ggagtacagt
1321 gttgatccat g

SEQUENCE LISTING

<160> NUMBER OF SEQ ID NOS: 4

<210> SEQ ID NO 1
<211> LENGTH: 1844
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
tgtcaagctt tcaacgcaca tgttttatga tgtatttta aatggtcgat accaacaatt      60
gatacatcag taagttgagc attacagaaa tgccaatagg tggcatacct tatcttctca     120
cgattgacgt ctttgaacaa ccattcgaag tcgtttcgta catcatgggt gctcttgcaa     180
cccttcttgt ggcaaacagt gttggtggct cgcgtgactg tggcttagct tcccaagaca     240
tcatcagcat tggtgggact tggggatcta caaatgaata cccacgttg tcatctcagg      300
gatatcagtc catggatgac aagacgttgt cacacgtcgc acaaccacat gaagtctttg     360
agacgggcaa catggaggac gggcaaggcc gcgtcgatgt gaaggacgga cgaggttaga     420
gaggacgagc gcaaccaagg aagatagcat aggccacgtc agtggcggat ccagaaacag     480
atcatgaggg ggctacgaaa ctaaagctat aaaattcttt taaaaaacaa tctaattgat     540
gttaatataa cacaattagc aagataaaac ttaaatactc aaaaggcatg tagcctaaat     600
aagtcggcac gaattctaca aatataataa taaataatca atacatatcg ttctgattct     660
tgataaggaa tatatccatc ctatccctat aaacataaaa tttaattta tcaactaacc      720
tactaaccta gcagataatt gattaaacca aaataccaaa taatctcacc ttcttattta     780
gcacagtagc tctagcagcc ccaggcacat agcaaactag cagcagaagc agtgcaaccg     840
gattcattgg ttcactttc atcaatcagc agggacaagg aggcttcacg aggtgtatag     900
catgctcaca catgacgcct ccacactcca cttcacggag cagccaacaa gcaccgagca     960
ggcgagcagc cagtgggggga ggcgacacct gattgagtcc tgatccctga tggagtgagg    1020
gagcgggact gaggacagcg gccggtgtgg gggaggacag gaggagccga gggcgcaggc    1080
tacactgccg atgtgccgca acgcgtgcgg gaggagccat gggcgcagcg cggacgtgca    1140
gtgcggaggg atgaagagcg gccagcagcg gctgggcgcg tgtgaagagg tgatgtgaga    1200
atctgaccta gctttttaga tttttatggg tcaaatttac tatatatcaa tgtttctaat    1260
ggaccacgat cggggctgca gcctggacag ccccgatcgc acatccaccc ctggcccagg    1320
tcataattgt cagccagaaa gaagatacat aaaagagatg acaaatatat ctcacatacc    1380
attttttaa taagattaaa tagcaaggga ttttctctac atagatctct tctatttct      1440
ttgttaccaa atcagctttg aaggtgcacc aacggaaaat ctgttcgccg cgtccatgac    1500
tcccagtccc tggtccctgc acgtctgcac tgtaccggca accccatccc catgcacaac    1560
acggctcaga ccccacgtac ctttttatcc ccctctttaa tgtgccacga tagcattaca    1620
cttccgcca tcatccatat gtcgtcgctc tcgttagaag caacggagct tatccatcgt    1680
tagtccgtta caacgatccg ccggcgccaa acgaccgccg gatccaatat aaataccctt    1740
```

```
gcacaggcat ggtgatcgac acacagccaa agtacaagac tcacttgcat ttttggcaca    1800
ccagcacaga agaagaaaaa aaaaacaggc actgagctga gatg                     1844

<210> SEQ ID NO 2
<211> LENGTH: 1370
<212> TYPE: DNA
<213> ORGANISM: Zea mays

<400> SEQUENCE: 2
aagcttaaag atcccattgg aagttaaact ctcggaaaga gttgatcgga tgttagacta      60
acttctgacg gtcgttgggg cccatcggaa gttagcgacg tagacgttgt tagcaccgaa     120
acttctaacc attttagtgg cctctcggaa gttattgtgc taacttccaa ggggtcccac     180
cggcttctca aaagttaatg tgctaacttc aggccatttt agtggcctct cgaaatttat     240
attgaaccaa cattcaaaat gttatttatt ttcaaatttc actatatttc aatacatcgg     300
gatacaaaca atcaggataa caacactaac tgcaatagca tctcatctgt ttcatcacaa     360
taacaccaca cctcataaat ctcatcaatt aaacacaatt ccaatatatt tcttcaaaat     420
aagaactcaa ttagtctcat ctcaacccaa gacacatccc aaatgtctta cagggttcac     480
aagttcacct cccatctatt tgaactatat cttatatatt aacaaacaac attagtttaa     540
atatcataca tttagttatg tctctttcct cattttact cgtagccatg attttgttt      600 agttttgcct cttctgctct tcagcaacag aataacaaaa ctgagtagaa aatacaacta     660
agggtaaaaa taaggaaagc ggtagaacta acggcaccac ttcaaaatgt cgtagtttaa     720
ataatttgat gttcatcaaa tactaaaatt caaaattaaa gacctctaga gtatattttt     780
cttacaagct ccagtggtgg ccgtgcctcg cgtggccata atcatcctta gtatgattga     840
tcatggacag ggtacagacc catgcttgac ttgataaaac accaacaata ccagacccca     900
tccccttccc tatcaacaac ggagggacga tgatatatta tttaggtctt gttcggatac     960
tctactatta tattcactct aaatcatatg tgttaatact agagtaccta aacaaggtct    1020
taagtgcatg cacgtgctgc acgctgttat ggacctatta ggtagtagta ggtcgagtag    1080
gatatatatc acaaagttgt ataccctataa atagctcgct ttgataacat gatctgctgc    1140
cttatacgaa acatagctac ctactactca agtatccatc cttattgtaa gtgctcttat    1200
aagctactac tagttacaag ctggtttata tttaactaca agtagcaacg atttgtctta    1260
gtatatatgg ttcataatac atatatattg gaactgagat aatatatgca ggagtacagt    1320
gttgatccat ggactcggaa ggagttgtag cagcaaaggt ggcagatgag               1370

<210> SEQ ID NO 3
<211> LENGTH: 1331
<212> TYPE: DNA
<213> ORGANISM: Zea mays

<400> SEQUENCE: 3
aagcttaaag atcccattgg aagttaaact ctcggaaaga gttgatcgga tgttagacta      60
acttctgacg gtcgttgggg cccatcggaa gttagcgacg tagacgttgt tagcaccgaa     120
acttctaacc attttagtgg cctctcggaa gttattgtgc taacttccaa ggggtcccac     180
cggcttctca aaagttaatg tgctaacttc aggccatttt agtggcctct cgaaatttat     240
attgaaccaa cattcaaaat gttatttatt ttcaaatttc actatatttc aatacatcgg     300
gatacaaaca atcaggataa caacactaac tgcaatagca tctcatctgt ttcatcacaa     360
taacaccaca cctcataaat ctcatcaatt aaacacaatt ccaatatatt tcttcaaaat     420
```

-continued

```
aagaactcaa ttagtctcat ctcaacccaa gacacatccc aaatgtctta cagggttcac      480
aagttcacct cccatctatt tgaactatat cttatatatt aacaaacaac attagtttaa      540
atatcataca tttagttatg tctctttcct cattttact cgtagccatg attttgttt        600 agttttgcct cttctgctct tcagcaacag aataacaaaa ctgagtagaa aatacaacta      660
agggtaaaaa taaggaaagc ggtagaacta acggcaccac ttcaaaatgt cgtagtttaa      720
ataatttgat gttcatcaaa tactaaaatt caaaattaaa gacctctaga gtatatttt      780 cttacaagct ccagtggtgg ccgtgcctcg cgtggccata atcatcctta gtatgattga     840
tcatggacag ggtacagacc catgcttgac ttgataaaac accaacaata ccagacccca    900
tccccttccc tatcaacaac ggagggacga tgatatatta tttaggtctt gttcggatac     960
tctactatta tattcactct aaatcatatg tgttaatact agagtaccta aacaaggtct    1020
taagtgcatg cacgtgctgc acgctgttat ggacctatta ggtagtagta ggtcgagtag   1080
gatatatatc acaaagttgt atacctataa atagctcgct ttgataacat gatctgctgc   1140
cttatacgaa acatagctac ctactactca agtatccatc cttattgtaa gtgctcttat   1200
aagctactac tagttacaag ctggtttata tttaactaca agtagcaacg atttgtctta   1260
gtatatatgg ttcataatac atatatattg gaactgagat aatatatgca ggagtacagt   1320
gttgatccat g                                                          1331
```

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

Lys Asp Glu Leu
1

MEANS AND METHODS OF CONTROLLING PLANT SEED GERMINATION

REFERENCE TO RELATED APPLICATION

This application claims priority pursuant to 35 U.S.C. §119(e) to previously filed and co-pending application U.S. Ser. No. 61/030,573, filed Feb. 22, 2008, the contents of which are incorporated herein by reference.

STATEMENT REGARDING FEDERALLY SPONSORED RESEARCH OR DEVELOPMENT

This invention was made with Government support under Grant No. 2006-39454-17450, awarded by U.S. Department of Agriculture. The Government has certain rights in the invention.

BACKGROUND

Biotechnology has grown into a multibillion industry with the vast majority of revenues coming from the production of transgenic proteins in recombinant hosts. To accommodate the growing demands and the continuing output of new transgenic products, many different protein production platforms have been established each with its own unique set of characteristics. Even with the vast array of available choices, many products are still limited by production costs to meet economic targets.

Plants have recently emerged as yet another production platform for protein production. Plants offer the potential advantages of 1) a non-animal source of protein reducing fears of pathogens, 2) reduced investment capital for equipment and facilities, 3) lower cost of goods, 4) rapid scale-up, 5) long term storage and transport at ambient temperatures, and 6) an alternative eukaryotic expression system that allows for posttranslational modifications (1). It is predictable that there will be certain products that may only be commercialized using the benefits that plant production systems can offer. It also seems predictable that there will not be one plant system that will be ideal for all the diverse applications of potential products.

While there are many options within plants, the need for low cost and large volumes quickly turns the focus to commodity crops. Commodity crops have been used for centuries as an excellent source of industrial and human health products as well as food and feed. For the most part, this practice has gone unnoticed by the public until the recent introduction of transgenic plants. The potential for nonfood transgenic products to be made in commodity crops has raised concerns over their intermixing with the food supply.

There are a number of approaches that can be used to reduce the risk of intermixing nonfood with food crops. The USDA has developed guidelines outlining management practices that must be followed when growing plants for nonfood uses (2). These dictate a closed loop system rather than an open system used for commodity products. The basic premises are similar to that used for other pharmaceutical production systems. The specifics vary for each crop but in general these restrictions include among others:

1. Physical isolation: food crops must not be grown in the vicinity of nonfood crops.
2. Temporal isolation: transgenic crops are delayed in the time of planting from commodity crops to reduce the possibility of out crossing.
3. Volunteer control: no food crop can be grown on the same acreage the years following the growing of the nonfood crop until all volunteers are accounted for.
4. Dedicated equipment: planting, harvesting, storage and transport equipment must not be used for food or feed crops.
5. Chain of custody: documentation accountability of the crop through its lifetime.
6. Monitoring: audit and inspection by third parties.

Adherence to these guidelines will prevent inadvertent exposures but as with any system, there is always a concern that human error or natural disasters will disrupt the system and place the transgenic crop into an uncontrolled environment.

In order to realize the benefits of plant production systems, there must be confidence that intermixing of the nonfood product with the food supply does not occur at any step in the manufacturing process. There are many steps in the process that must be addressed and most of the contamination concerns are similar to those facing non-plant host organisms for protein production. It is the potential for contamination of the seed that has raised most of the concern for plant-based protein production. Contamination could come about by unintended cross-pollination in neighboring fields of food crops, by the inadvertent spillage of seed into fields of food crops or by volunteer seed from the previous season.

All of these concerns have been addressed in USDA guidelines that outline management practices to prevent inadvertent exposure. In spite of these precautionary measures, there is still concern that as the acreage and the number of products increase, there is a greater likelihood of mishaps due to natural disasters or human error. This concern has led to a fear of using plants as a host for nonfood products which has delayed or prevented the introduction of useful products.

Keeping crops enclosed inside buildings such as greenhouses, caves, or cell culture fermentors has been proposed to alleviate some concerns associated with using field grown crops. This can be a very viable strategy for higher cost and smaller volume products. This practice, however, is not suitable for rapid scale-up or large volumes. These systems can easily raise the cost of the product well beyond practical economic restraints thereby eliminating any other advantage that may be derived using plants.

One approach previously attempted to genetically control germination has been called the "terminator technology". This approach has already been demonstrated to work in tobacco but has been met with controversy (26) arising from the implication that growers are forced to buy new seed each year from suppliers rather then saving part of their crop from the previous season to be used as seed. This situation, however, only applies to commodity crops grown as varieties and should not be a concern for specialty-regulated crops. Moreover, it does not apply to corn which is grown as a hybrid crop and growers already buy new seed each year. Therefore, it seems reasonable that the concerns with the public perception may be eliminated regarding this specific technology with a campaign to educate the public in the new uses.

The second limitation of using terminator technology is the technical complexity of the system. This approach requires a toxin, a repressor protein, a chemically induced promoter, a recombinase system and multiple transformations of the same plant (27). While there is no reason to believe this will not work in other plants including corn, it is much more complex than inserting a single gene. This leads to a practical limitation in that it is difficult to use this routinely for new genes in discovery, adding significant time and capital to product development. It is therefore unlikely that product developers will use this system initially on nonfood products.

Another proposed solution is to use only nonfood crops for the production of transgenic nonfood products. The prospect that using a nonfood host may solve the public perception problems for plants is in contradiction to what is in practice for other non-plant hosts. There is substantial precedent in non-plant systems for safe production of nonfood products in food organisms. Examples include eggs and yeast that are routinely used to produce industrial enzymes, vaccines and therapeutics. The public has accepted this with regulatory oversight realizing that the risks are insignificant compared to the benefits. The key issue is not whether a food crop, nonfood crop or laboratory system is used to produce the transgenic protein products but rather what measures are in place to prevent inadvertent contamination of the food supply and whether the products can be produced economically.

Many of the same potential problems exist when field grown crops are used as hosts whether they are food or nonfood crops. In particular, inadvertent disposition of seed from non-food crops can result in intermixing with food crops and pose the same threat as transgenic products produced in food crops.

The use of nonfood crops also presents added safety concerns when making final products as they do not have GRAS (generally regarded as safe) status. Many nonfood plants contain toxins and carcinogens (e.g. tobacco) which need to be accounted for in the final product. The advantage of using food crops is readily apparent for such potential products as orally delivered vaccines where the final product is not purified and is taken in a processed form of the crop.

Current management practices for growing regulated transgenic crops can be expensive when factoring the cost of monitoring not only the immediate growing area but also the surrounding area for displaced seed. This could include volunteers for up to several years and miles from the initial planting, the specific time and distance determined by the specific characteristics of the crop.

One approach to containment that has proven successful with microorganisms is to have a genetically crippled host such that the organisms cannot reproduce on their own without human intervention. This has been applied to a number of different microorganisms including *E. coli* which has led to the use of specific strains that are used routinely in laboratory operations with minimal physical containment practices because of the confidence and experience that has been obtained over time.

SUMMARY OF THE INVENTION

Control of germination of a plant seed is provided by introducing into the plant seed a nucleic acid molecule encoding a germination inhibiting protein with expression directed by a promoter conferring expression during germination. An embodiment provides the germination inhibition protein action is reversed by exposure to a restoring substance. A preferred embodiment provides the restorer reverses germination inhibition of the protein and is applied when seed germination is desired. In another embodiment the promoter is selected from the group consisting of alpha amylase or phytase promoters. In another embodiment the growth inhibiting protein is selected from avidin or streptavidin. Also provided is an amylase germination preferred promoter.

BRIEF DESCRIPTION OF THE DRAWINGS

FIG. 6 shows the sequence of an alpha amylase promoter (SEQ ID NO: 1), with the ATG start site underlined.

FIG. 7 shows the phytase promoter sequence with the intron (SEQ ID NO: 2) and without the intron (SEQ ID NO: 3). The ATG site is underlined and in bold.

DESCRIPTION OF EMBODIMENTS FO THE INVENTION

Our objective is to develop genetically crippled plants that will not germinate on their own. In concept these genetic lines would provide safeguards and advantages similar to those that have been used for production of nonfood products in microorganisms and have allowed their widespread use without undue concern for contamination.

Having two genetically different but related crops, one for food and one for industrial applications, is the situation that exists for rapeseed today. In this case, one crop is used for industrial purposes and a different crop is used for food applications (i.e. canola oil). However, the industrial crop in this proposal would go beyond the practice of segregation and include key genetic features that will limit inadvertent exposure.

Germination occurs when the seed resumes growth. Typically, it begins with resumption of growth of the embryo through appearance of a radicle outside the seed coat. Without germination, no plant will mature. Seed that is incapable of germination can provide a genetic solution redundant to management practices for preventing inadvertent mixing in food crops. Seed spilled during transport, relocated by tornadoes or wild animals must be accounted for and not allowed to germinate or mature for future pollinations. Therefore, experiments are outlined to demonstrate control of seed germination. We anticipate the other traits listed above for industrial maize will be added to the germplasm to enhance the features of industrial maize and fulfill our long-term goal.

Figure 1:
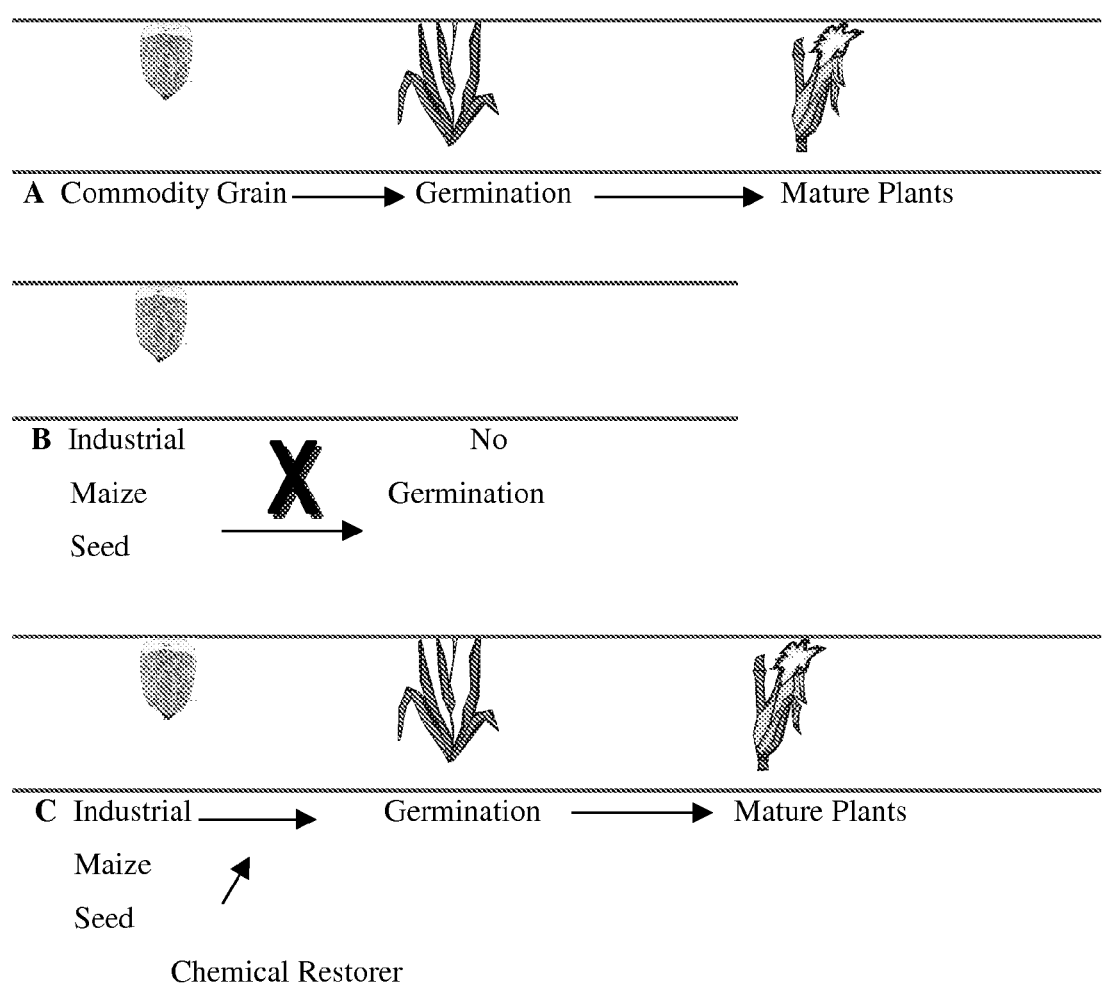
FIG. 1 shows a flow chart of a chemically induced seed germination system. Control of germination under different scenarios is shown: A) Commodity grain can germinate under normal environmental conditions; B) Industrial maize cannot germinate under normal environmental conditions; and C) Industrial maize pretreated with a specific chemical that will allow germination.

The approach we have taken to prevent germination is to express a germination/growth inhibiting protein under the control of a promoter that confers expression preferentially during germination. The germination preferred promoter may express during germination along with expression at other stages or may express strongly only during germination and to a much lesser degree at other times. The degree of "leakiness" tolerated will depend upon the toxicity of the growth inhibiting protein encoding molecule. The action of this growth inhibiting protein would then be reversed by a chemical treatment. A chemical restorer that reverses the toxic action of the protein during germination could be applied as a seed treatment only when it is desired for the seeds to germinate. The simplicity of this system allows for the possibility of routinely including it as part of the initial transformation vector along with the gene of interest in the same way as selectable markers are integrated. This would also allow the germination to be directly linked to the expression of the transgenic protein of interest. In theory there would be no germination of the transformed seeds unless they were pretreated with the restorer chemical (FIG. 1).

It will be evident to one skilled in the art that various methods and components may be useful in the invention. The following is provided by way of illustration and not limitation of the many techniques and components that could be used in the invention. All references cited are incorporated herein by reference.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, Brassica, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses. Reference to "food plant" means a plant which can be consumed by an animal.

The plant tissue used may be that of the original plant transformed with the sequence of interest, or can be a descendant obtained by crossing with the same plant or another plant, as described in the methods below.

The use of the term "nucleotide constructs" and "nucleic acids" herein is not intended to limit the present invention to nucleotide constructs comprising DNA. Those of ordinary skill in the art will recognize that nucleic acid molecules, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like. By referring to a "heterologous" nucleic acid is meant that the nucleic acid has been introduced into the plant by human intervention, such as by transformation with a nucleotide sequence, crossing or backcrossing with another plant transformed with the nucleotide sequence, infection of the plant through bacterial or viral methodology, or the like.

The invention uses a sequence having a germination-inhibiting effect that is reversible. The protein in a preferred embodiment is one in which the inhibiting effects of the protein are capable of being reversed by exposure to a restoring substance. In referring to germination inhibition or growth inhibition is meant any protein that is capable of preventing germination of the plant seed. By inhibiting germination a plant will not form from the seed. Examples of such growth inhibiting proteins include without limitation proteins that interfere with general metabolism such as proteases, lipases or glycosidases and proteins that target specific metabolic pathways that are critical for growth and where the inhibiting effect is reversible by application of a restoring substance. Protease inhibitors nullify the action of proteases as discussed infra. Lipase and glycosidase can also be nullified. Two chemical inhibitors of lipases are ETYA and HELSS (Holk et al., *Plant Phys* (2002) 130:90-101 and p-chloromercuribenzoic acid (Ory et al., *J. Lipid Research* (1960) 1:208-213 Two general chemical inhibitors of glycosidases are castanospermine (Molyneux et al. *J Nat Prod* (1990) 53:609-614) and deoxynojirimycin/Bay m1099 (Joubert et al. *Eur. J. Clin. Pharmacol* (1985) 28:705-708). BASI and RASI are bifunctional in that they seem to be able to target both endogeneous alpha amylases and subtilisins from pathogens. They may be involved in both regulation of germination and defense against pathogens. By way of example without limitation such nucleic acid sequences include a barley alpha-amylase/subtilisin inhibitor (BASI) (Leah et al. *Plant Mol Biol* (1989) 12:673-682; Furtado et al. *Plant Mol Biol* (2003)52: 787-799); rice alpha-amylase/subtilisin inhibitor (RASI) (Ohtsubo et al. *FEBS Lett.* (1992) 309:68-72; Yamagata et al. *Biosci Biotechnol Biochem* (1998)62:978-985); the barley hvWRKY38 protein, which has been proposed to act downstream of salicylic acid and ABA in suppressing germination (Xie et al. *Plant Mol Biol* (2007) 64:293-303); and wheat PKABA1 to mediate ABA suppression of alpha-amylase expression (Anderberg et al. *Proc. Natl. Acad. Sci* (1992) 89:10183-10187) Gomez-Cadenas et al. *Plant Cell* (2001) 13:667-679). There are many general protein kinase inhibitors. One example is H89 (*Cardiovasc Drug Res* (2006) 24:261-274). The action of these proteins can then be reversed by the addition of a restoring substance. This restoring substance is any substance which can reverse the germination inhibition effect of the germination inhibition protein. As an example in the case of a protease, a protease inhibitor can be applied to negate the activity of the protease. By way of example, without limitation, trypsin is a protease, the sequence of which has been well characterized. See Greaney, EP 0 587 681. The protease action of trypsin can be counteracted by a trypsin protease inhibitor, which has also been well characterized from corn and soybean, for example. In another example, sequences encoding avidin are used (See U.S. Pat. No. 5,767,379) or streptavidin, (See Argarana et al., (1986) *Nucleic Acids Res.,* 14(4): 1871-1882 (1986) and Guan et al. (1993) *Plant Physiol*. vol. 102, pl. 45), which encodes a protein which inhibits growth, the effects of which can be reversed by exposure to biotin.

The expression vector of the germination inhibiting protein can in one embodiment also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Various cell components can be targeted in this manner. By way of example without limitation, such targeting can include directing expression to the cytoplasm, cell wall, vacuole, chloroplast, peroxisomes, endoplasmic reticulum, mitochondria, or any of a variety of cell components or to be secreted from the cell. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3-17 (1987), Lerner et al., *Plant Physiol.* 91:124-129 (1989), Fontes et al., *Plant Cell* 3:483-496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499-509 (1984), Steifel, et al., Expression of a maize cell wall hydroxyproline-rich glycoprotein gene in early leaf and root vascular differentiation, *Plant Cell* 2:785-793 (1990). As further described below, more than one signal sequence in a preferred embodiment can be used to target the protein to more than one cell component.

When targeting the protein to the cell wall use of a signal sequence is necessary. An example of such signal sequences useful in the invention are alpha amylase sequences. One example is the barley alpha-amylase signal sequence (Rogers, J. C. 1985. Two barley alphaamylase gene families are regulated differently in aleurone cells. *J. Biol. Chem.* 260: 3731-3738). In a one embodiment, the growth inhibiting protein is expressed in the endoplasmic reticulum of 25 the plant cell. This may be accomplished by use of a localization sequence, such as KDEL (SEQ ID NO: 4). This sequence (Lys-Asp-Glu-Leu (SEQ ID NO: 4)) contains the binding site for a receptor in the endoplasmic reticulum. (Munro, S. and Pelham, H. R. B. 1987 "A C-terminal signal prevents secretion of luminal ER proteins" *Cell* 48:899-907. The use of such a localization sequence will increase expression over levels obtained when the enzyme is otherwise expressed in the cytoplasm.

Targeting the protein to the vacuole is another option. Signal sequences to accomplish this are well known. For example, Raikhel U.S. Pat. No. 5,360,726 shows a vacuole signal sequence as does Warren et al at U.S. Pat. No. 5,889, 174. Vacuolar targeting signals may be present either at the amino-terminal portion, (Holwerda et al., *The Plant Cell*, 4:307-318 (1992), Nakamura et al., *Plant Physiol.*, 101:1-5 (1993)), carboxy-terminal portion, or in the internal sequence of the targeted protein. (Tague et al., *The Plant Cell*, 4:307-318 (1992), Saalbach et al. *The Plant Cell*, 3:695-708 (1991)). Additionally, amino-terminal sequences in conjunction with carboxy-terminal sequences are responsible for vacuolar targeting of gene products (Shinshi et al. *Plant Molec. Biol.* 14:357-368 (1990)).

The nucleotide constructs of the invention encompass expression cassettes for expression in the plant of interest. The cassette will include 5' and 3' regulatory sequences operably linked to a nucleotide sequence encoding a polysaccharide-degrading enzyme of the invention. By "operably linked" is intended a functional linkage between a promoter and a second sequence, wherein the promoter sequence initiates and mediates transcription of the nucleotide sequence corresponding to the second sequence. Generally, operably linked means that the nucleotide sequences being linked are contiguous and, where necessary to join two protein coding regions, contiguous and in the same reading frame. Promoter elements employed to control expression of protein and the selection gene, respectively, can be any plant-compatible promoter.

Further employed in the invention is a promoter that will direct expression of the protein during germination. We refer to these as germination preferred promoters, meaning they express at higher levels during germination than during other stages of the plant development. These can also be referred to as germination tissue-specific or germination temporal-specific promoters meaning the promoter directs expression at high levels during germination of the seed. As discussed supra, how much expression in other stages of development is preferred will depend upon the potential for toxicity of the germination inhibiting protein to impact non-germinating tissue. An example of one such promoter is the alpha amylase gene promoters. Starch includes straight-chain starch and branched starch, two types of polysacchardies, and is the basic stored nutrient component in cereal grains. Alpha-amylases break down starch 1-4 linkages During the initial germinating period of cereal seeds, the aleurone layer cells will synthesize alpha-amylase to provide the nutrients needed for the growth of the germ. Some of the best-characterized promoters active during germination are those isolated from the barley amylase genes (18). Phytase promoters are yet another example. Phytase is digestive enzyme which is present in the digestive systems of many plant-eating animals to enable breakdown of phytate (also known as "phytic acid") and is sometimes present within the plant material consumed by animals. Various phytase promoters are known to one skilled in the art, such as those discussed, for example at Bower U.S. Pat. No. 7,499,317. These are examples of promoters preferentially expressing during germination. Yet other examples, without intending to be limiting, are maize CCP2 (*Biochim Biophys Acta* (1995)1263:241-244), barley beta glucanase isoenzyme EII (*Plant Phys* (1992) 99:1226-1231), and tomato expansin (*Plant Phys* (2001) 127:928-936).

In the methods of the invention, a number of promoters that direct expression of a gene in a plant can be employed when used, for example, with a selectable or scorable marker. Such promoters can be selected from constitutive, chemically-regulated, inducible, and tissue-preferred promoters. Constitutive promoters include, for example, the core CaMV 35S promoter (Odell et al. (1985) *Nature* 313:810-812); ubiquitin promoters (Quail et al., U.S. Pat. No. 5,510,474; ubiquitin-like promoters (Jilka et al. US Publication 20030066108); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730), and the like. Other constitutive promoters include, for example, those described at U.S. Pat. Nos. 5,608,149; 5,608,144; 5,604,121; 5,569,597; 5,466,785; 5,399,680; 5,268,463; and 5,608,142.

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the instant invention. See Ward et al. (1993) Plant Mol. Biol. 22: 361-366 (1993). Exemplary inducible promoters include ecdysone receptor promoters, U.S. Pat. No. 6,504,082; promoters from the ACE1 system which responds to copper (Mett et al. PNAS 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227: 229-237, and U.S. Pat. Nos. 5,814,618 and 5,789,156).

Tissue-preferred promoters can be utilized to target enhanced transcription and/or expression within a particular plant tissue. When referring to preferential expression, what is meant is expression at a higher level in the particular plant tissue than in other plant tissue. Examples of these type of promoters include seed preferred expression such as that provided by the phaseolin promoter (Bustos et al. 1989. *The Plant Cell* Vol. 1, 839-853), and the maize globulin-1 gene, Belanger, et al. 1991 *Genetics* 129:863-972. For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. there are a wide variety of tissue-preferred promoters and, by way of example, include those described in Yamamoto et al. (1997) *Plant J.* 12(2): 255-265; Kawamata et al. (1997) *Plant Cell Physiol.* 38(7): 792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20: 181-196; Orozco et al. (1993) *Plant Mol Biol.* 23(6): 1129-1138; Matsuoka et al. (1993) *Proc Natl. Acad. Sci. USA* 90(20): 9586-9590.

Selectable reporter genes for selection of transformed cells or tissues can be included in the transformation vectors. These can include genes that confer antibiotic resistance or resistance to herbicides. Examples of suitable selectable marker genes include, but are not limited to, genes encoding resistance to chloramphenicol, Herrera Estrella et al. EMBO J. 2:987-992 (1983); methotrexate, Herrera Estrella et al. *Nature* 303:209-213 (1983); Meijer et al. Plant Mol. Biol. 16:807-820 (1991); hygromycin, Waldron et al. *Plant Mol. Biol.* 5:103-108 (1985), Zhijian et al. *Plant Science* 108:219-227 (1995); neomycin phosphotransferase confers resistance to kanamycine (See, e.g., Fraley et al, (1983) *Proc. Natl. Acad. Sci. USA* 80:4803; Miki et al. (1993) "Procedures for Introducing foreign DNA into plants" *Methods in Plant Molecular Biology and Biotechnology"*, Glick et al. (eds.) pp. 67-68 (CRC Press 1993; streptomycin, Jones et al. *Mol. Gen. Genet.* 210:86-91 (1987); spectinomycin, Bretagne-Sagnard et al. Transgenic Res. 5:131-137 (1996); bleomycin, Hille et al. *Plant Mol. Biol.* 7:171-176 (1990); sulfonamide, Guerineau et al. *Plant Mol. Biol.* 15:127-136 (1990); bromoxynil, Stalker et al. *Science* 242:419-423 (1988); glyphosate, Shaw et al. *Science* 233:478-481 (1986); and phosphinothricin, DeBlock et al. *EMBO J.* 6:2513-2518 (1987). The latter is the phosphinothricin acetyl transferase ("PAT") or maize optimized PAT or bar gene confers resistance to bialaphos (Gordon-Kamm. 1990. *The Plant Cell* 2: 603; Uchimiya et al. 1993. Bio/Technology 11: 835; and Anzai et al, 1989. *Mol. Gen. Gen.* 219: 492).

Scorable or screenable markers may also be employed, where presence of the sequence produces a measurable product. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The *EMBO Journal* vol. 6 No. 13 pp. 3901-3907); and alkaline phosphatase. Other screenable markers include the anthocyanin/flavonoid genes in general (See discussion at Taylor and Briggs, *The Plant Cell* (1990) 2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., *Plant Cell* (1996) 8: 1171-1179; Scheffler et al. *Mol. Gen. Genet.* (1994) 242:40-48) and maize C2 (Wienand et al., *Mol. Gen. Genet.* (1986) 203:202-207); the B gene (Chandler et al., *Plant Cell* (1989) 1:1175-1183), the p1 gene (Grotewold et al, *Proc. Natl. Acad. Sci USA* (1991) 88:4587-4591; Grotewold et al., *Cell* (1994) 76:543-553; Sidorenko et al., *Plant Mol. Biol.* (1999) 39:11-19); the bronze locus genes (Ralston et al., *Genetics* (1988) 119:185-197; Nash et al., *Plant Cell* (1990) 2(11): 1039-1049), among others. Yet further examples of suitable markers include the cyan fluorescent protein (CYP) gene (Bolte et al. (2004) *J. Cell Science* 117: 943-54 and Kato et al. (2002) *Plant Physiol* 129: 913-42), the yellow fluorescent protein gene (PhiYFP™ from Evrogen; see Bolte et al. (2004) *J. Cell Science* 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343); a green fluorescent protein (GFP) gene (Sheen et al., *Plant J.* (1995) 8(5):777-84); and DsRed genes where plant cells transformed with the marker gene are red in color, and thus visually selectable (Dietrich et al. (2002) *Biotechniques* 2(2):286-293). Additional examples include a β-lactamase gene (Sutcliffe, *Proc. Nat'l. Acad. Sci. U.S.A.* (1978) 75:3737), which encodes an enzyme for which various chromogenic substrates are known (e.g., PADAC, a chromogenic cephalosporin); a xylE gene (Zukowsky et al., *Proc. Nat'l. Acad. Sci. U.S.A.* (1983) 80:1101), which encodes a catechol dioxygenase that can convert chromogenic catechols; an α-amylase gene (Ikuta et al., *Biotech.* (1990) 8:241); and a tyrosinase gene (Katz et al., *J. Gen. Microbiol.* (1983) 129: 2703), which encodes an enzyme capable of oxidizing tyrosine to DOPA and dopaquinone, which in turn condenses to form the easily detectable compound melanin. Clearly, many such markers are available to one skilled in the art.

In addition to a promoter, the expression cassette can include one or more enhancers. By "enhancer" is intended a cis-acting sequence that increases the utilization of a promoter. Such enhancers can be native to a gene or from a heterologous gene. Further, it is recognized that some promoters can contain one or more native, enhancers or enhancer-like elements.

The termination region can be native with the transcriptional initiation region, can be native with the operably linked DNA sequence of interest, or can be derived from another source. Convenient termination regions are available from the Ti-plasmid of *A. tumefaciens*, such as the octopine synthase and nopaline synthase termination regions. In one embodiment of the invention the pin II terminator from the protease inhibitor II gene from potato (An et al., 1989. Functional analysis of the 3' control region of the potato wound-inducible proteinase inhibitor II gene. *Plant Cell* 1:115-122) is used. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, 5,436,391, and Murray et al. (1989) *Nucleic Acids Res.* 17:477-498.

Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes can additionally contain 5'-leader sequences in the expression cassette construct. Such leader sequences can act to enhance translation. Translation leaders are known in the art and include but are not limited to: picornavirus leaders, for example, potyvirus leaders such as the TEV leader (Tobacco Etch Virus) (Allison et al. (1986); MDMV leader (Maize Dwarf Mosaic Virus); *Virology* 154: 9-20), untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Czech (Liss, New York), pp. 237-256); and maize chlorotic mottle virus leader (MCMV) (Lommel et al. (1991) *Virology* 81:382-385). Other methods known to enhance translation can also be utilized, for example, introns, and the like.

In preparing the nucleotide construct, the various DNA fragments can be manipulated, so as to provide for the DNA sequences in the proper orientation and, as appropriate, in the proper reading frame. Toward this end, adapters or linkers can be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Obviously, many variations on the promoters, selectable markers, signal sequences and other components of the construct are available to one skilled in the art.

The methods available for construction of recombinant genes comprising various modifications for improved expression described above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene is engineered to contain desired features, such as the desired localization sequences, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context will encode the growth inhibiting protein; eukaryotic DNA elements that control initiation of transcription of the exogenous gene, such as a promoter; and DNA elements that control the processing of transcripts, such as transcription termination/polyadenylation sequences. It also can contain such sequences as are needed for the eventual integration of the vector into the plant chromosome.

In accordance with the present invention, a transgenic plant is produced that contains a DNA molecule, comprised of elements as described above, integrated into its genome so that the plant expresses a heterologous growth inhibiting-encoding DNA sequence expressed during germination. In order to create such a transgenic plant, the expression vectors containing the gene can be introduced into protoplasts, into intact tissues, such as immature embryos and meristems, into callus cultures, or into isolated cells. Preferably, expression vectors are introduced into intact tissues. General methods of culturing plant tissues are provided, for example, by Miki et al. 1993. "Procedures for Introducing Foreign DNA into Plants" in *Methods in Plant Molecular Biology and Biotechnology*, Glick et al (eds) CRC Press pp. 67-68 and by Phillips et al. 1988 "Cell/Tissue Culture and In Vitro Manipulation" in *Corn and Corn Improvement* 3d Edit. Sprague et al (eds) American Soc. of Agronomy pp. 345-387. The selectable marker incorporated in the DNA molecule allows for selection of transformants.

Methods for introducing expression vectors into plant tissue available to one skilled in the art are varied and will depend on the plant selected. Procedures for transforming a wide variety of plant species are well known and described throughout the literature. See, for example, Miki et al, supra; Klein et al. 1992. *Bio/Technology* 10:26; and Weisinger et al., 1988. *Ann. Rev. Genet.* 22: 421-477. For example, the DNA construct may be introduced into the genomic DNA of the plant cell using techniques such as microprojectile-mediated delivery (Klein et al. 1987. *Nature* 327: 70-73); electroporation (Fromm et al. 1985. *Proc. Natl. Acad. Sci.* 82: 5824); polyethylene glycol (PEG) precipitation (Paszkowski et al. 1984. *Embo J.* 3: 2717-272); direct gene transfer (WO 85/01856 and EP No. 0 275 069); in vitro protoplast transformation (U.S. Pat. No. 4,684,611) and microinjection of plant cell protoplasts or embryogenic callus (Crossway, 1985. *Mol. Gen. Genetics* 202:179-185). Co-cultivation of plant tissue with *Agrobacterium tumefaciens* is another option, where the DNA constructs are placed into a binary vector system (Ishida et al. 1996. "High Efficiency Transformation of Maize (*Zea mays* L.) Mediated by *Agrobacterium tumefaciens*". *Nature Biotechnology* 14:745-750). The virulence functions of the *Agrobacterium tumefaciens* host will direct the insertion of the construct into the plant cell DNA when the cell is infected by the bacteria. See, for example Horsch et al. 1984. *Science* 233: 496-498, and Fraley et al. 1983. *Proc. Natl. Acad. Sci.* 80: 4803.

Standard methods for transformation of canola are described by Moloney et al. 1989. "High Efficiency Transformation of *Brassica napus* Using *Agrobacterium* Vectors" *Plant Cell Reports* 8:238-242. Corn transformation is described by Fromm et al, 1990. *Bio/Technology* 8:833 and Gordon-Kamm et al, supra. *Agrobacterium* is primarily used in dicots, but certain monocots such as maize can be transformed by *Agrobacterium*. U.S. Pat. No. 5,550,318. Rice transformation is described by Hiei et al. 1994. "Efficient Transformation of Rice (*Oryza sativa* L.) Mediated by *Agrobacterium* and Sequence Analysis of the Boundaries of the T-DNA" The Plant Journal 6(2): 271-282, Christou et al. 1992. *Trends in Biotechnology* 10:239 and Lee et al. 1991. *Proc. Nat'l Acad. Sci.* USA 88:6389. Wheat can be transformed by techniques similar to those used for transforming corn or rice. Sorghum transformation is described by Casas et al., 1997. Transgenic sorghum plants obtained after microprojectile bombardment of immature inflorescences. In vitro cellular and developmental biology, *Plant*. 33:92-100 and by Wan et al. 1994. *Plant Physiology*. 104:37. Soybean transformation is described in a number of publications, including U.S. Pat. No. 5,015,580.

In one method, the *Agrobacterium* transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi-II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid.

Further, the Ishida protocol as described provides for growing fresh culture of the *Agrobacterium* on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 and is preferably between 0.2 and 0.5. The bacteria are then centrifuged to remove the media and resuspended in the co-culture medium. Since Hi-II is used, medium preferred for Hi-II is used. This medium is described in considerable detail by Armstrong, C. I. and Green C. E. 1985. Establishment and maintenance of friable, embryogenic maize callus and involvement of L-proline. *Planta* 154: 207-214. The resuspension medium is the same as that described above. All further Hi-II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art. For a discussion of plant breeding techniques, see Poehlman (1995) *Breeding Field Crops*. AVI Publication Co., Westport Conn., 4$^{th}$ Edit. Backcrossing methods may be used to introduce a gene into the plants. This technique has been used for decades to introduce traits into a plant. An example of a description of this and other plant breeding methodologies that are well known can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

EXAMPLES

The following presents examples of methods of analysis employed in the use of the invention and experimental procedures regarding same. It is intended to be illustrative and not limiting to the invention.

Example—Avidin as a Reversible Inhibitor of Germination

The ideal protein of choice for this system would be highly effective in inhibiting the growth of plant cells, easily expressed in plant cells and have known substances that can completely reverse the action. The ideal substance would also be one that is known to be safe to humans, easily taken up by plants, readily available and inexpensive to add as a seed treatment. There are several candidates in theory, but we have identified one combination that shows great promise for the characteristics outlined above. This system uses the protein avidin, found naturally in chicken eggs. Avidin binds extremely tightly to biotin, a B vitamin, and reduces the amount of free biotin in the cell resulting in the inhibition of growth (16). The addition of excess biotin can reverse this inhibition.

The avidin gene has been previously transformed into corn plants. See for example U.S. Pat. No. 5,767,379. When avidin was targeted for expression in the cytoplasm with a constitutive promoter, it inhibited the production of transgenic plants (unpublished results). However, avidin targeted to the cell walls resulted in high levels of expression presumably by sequestering the avidin from other cellular activity (17). Therefore, avidin appears to be an excellent choice in that 1) it is a natural protein already in the food supply; 2) it can be expressed in plant cells; 3) it can inhibit plant growth when expressed in the cytoplasm; 4) it has low human toxicity; and 5) its activity can be completely reversed with a simple chemical.

Biotin is a B vitamin and provides a safe chemical for seed treatment. In addition, biotin is inexpensive and readily available. Biotin has been shown to completely reverse the effect of avidin in many systems. More importantly, it has been shown to reverse the effect in vivo in corn. When avidin was expressed in corn plants with a constitutive promoter targeted to the cell wall, male sterility occurred (14). The application of biotin to these plants was able to reverse the effect of avidin and render the plants fertile (unpublished results). This demonstrated that biotin can be readily absorbed by plant tissue and used to reverse the effect in vivo on corn.

Example—Germination Preferred Promoter

The last requirement of this system is a promoter that will direct expression of the protein only during germination. As noted, the barley amylase genes are active during germination (18). These have been classified as either the high or low pI types. Both types have been shown to have good expression during germination but the low pI genes also show expression in other stages of development. We have thus focused on the high pI group that has greater specificity for germination. Expression of these high PI promoters was not observed in the leaves, stems or roots of older tissue (19). More critically for our proposed system, when seeds were bisected, only the half imbibed in water conferred expression while no expression could be seen in the dry seeds indicating the specificity of this promoter to germination (20).

Monocot promoters from one species have been shown to work in other monocot species. These include the barley amylase promoters that have been shown to be active in maize tissue (21, 22). Based on our own experience with monocot promoters and the reports in the literature, we would anticipate that the barley high pI amylase promoter would be suitable for the feasibility study in maize. There is also an analogous amylase gene from maize that has been isolated and sequenced that can be used to isolate the corresponding maize promoter (23).

In this proposed system, seeds obtained from the transformed plants would not germinate unless they were treated with biotin. Biotin treated seed would be used for conventional breeding operations and to make seeds used for the production of the industrial or pharmaceutical protein. In the event that any seed was spilled during transport, relocated due to animals or left on the field for any reason, the progeny of the biotin treated seed would not germinate on its own.

Example—Maize as a Model Crop

The use of genetically crippled plants makes sense for any field grown crop producing nonfood products whether or not it is already in the food chain. It can also be used for experimental food crops to avoid the possible escape of genes prior to deregulation. One of the crops at the forefront of transgenic plants for food, feed, pharmaceutical and industrial applications is maize. Maize is one of the most widely grown crops in the world particularly in North America. It can be grown in a wide spectrum of climates producing high yields. Maize is a very convenient and inexpensive source of grain which is well suited for a variety of uses, most notably animal feed, which accounts for the majority of the grain produced today. Corn is also used as a source of food that people consume directly such as sweet corn and popcorn and it is further used in a wide variety of processed foods.

Industrial uses of maize have not generated much attention until recently. One of the more recent expansions in industrial applications is the conversion of cornstarch into fermentable sugars that in turn can be used in the production of ethanol. Ethanol was seen first as a fuel additive to help lower pollution and some states have provided incentives to offer a 10% blend of ethanol with conventional gasoline. Higher gasoline prices now provide an economic incentive for ethanol as a substitute for gasoline. The United States has seen an increase from 175 million barrels of ethanol produced from corn in 1980 to over 3 billion barrels accounting for 15% of the total corn production (3).

There are many other industrial uses of corn that are also expanding, primarily for starch, organic acids, polyols and other chemicals. More than 500 million pounds of industrial chemicals are produced annually from corn, which is a five-fold increase since 1980 (4). Moreover, several groups are now developing methods to convert corn stover rather than the grain into ethanol providing growers with added income without increasing acreage.

Corn may also be used as a host to provide transgenic proteins for industrial enzymes, therapeutic proteins and vaccines (5, 6, 7). The first of these products are already on the market (8) with many more under development. One of these potential applications includes the production of the enzymes needed for biomass conversion of corn stover into ethanol. Corn is an appropriate crop for this type of protein production as it requires extremely large volumes at very low cost. High expression of the key cellulase enzymes has recently been demonstrated in the germ fraction (9). It has been further proposed (10) to provide an integrated system using both maize grain and stover for ethanol with the enzymes being produced in the germ (non-starch fraction). Regardless of the specific applications, it is becoming clear that the transgenic industrial applications are placing more demands on corn production.

Growers in general have welcomed this new opportunity to increase the value of a crop that is has some key attributes that make it one of the better choices for a number of select products. These include:

Low cost of protein/grain
Generally Regarded As Safe (GRAS) status
Not known to contain highly allergenic, antinutritional or carcinogenic properties
Already used in many industrial applications
Adaptation to many growing areas
Several methods of pollen control including well developed male sterility system
No wild relatives in the United States eliminating outcrossing to weeds
Hybrid vigor providing a disincentive for growers to save seed and providing more control on the germplasm
Seed is only viable in the soil for the following season reducing the effect of escaping genes in subsequent years due to seed dormancy
Proteins can be stored in grain for years and retain activity
Relatively high protein content
Genetic variants readily available
Well-characterized system for transforming and expressing transgenic proteins
Well-established methods for grain processing
Demonstrated to be effective for oral delivery of vaccines
Demonstrated to be effective for direct delivery of industrial applications without purification
Established methods to easily extract proteins
Products have already been produced commercially In order to reduce public fears, increase the safety margin for field grown crops, and decrease the cost of containment, we describe the development of specialized industrial crops separate and distinct from commodity crops. Industrial maize would have several distinguishing genetic differences from the commodity crop that will reduce risks of intermixing with food corn and increase the economic value for protein production. These would include differences from commodity corn such as:

1) Preferential expression of transgenic proteins: Certain lines of corn have been shown to increase the expression of transgenic proteins preferentially (11) most likely due to metabolic, translation or transcription factors.
2) Higher protein content: Since the high value product is protein, providing grain that has higher protein content may be advantageous. There are lines of maize as high as 30% protein (12) compared to commodity corn at 9%.

3) Physical appearance of grain: The grain may have a distinct color or shape that could be easily recognizable from commodity corn. Many natural genetic markers exist that can be used to accomplish this (13). There are also a host of genes that could be transformed into corn specifically for this purpose.

4) Use of male sterile lines: This could be in the form of the widely used cytoplasmic male sterility systems (14) or nuclear encoded genes for sterility (15).

5) Distinct selectable marker system: The PAT gene confers glufosinate resistance which is used routinely to transform most maize plants. Herbicide treatment is an easy screening and selection tool used in the field but there is no distinction between transformed plants used for food or nonfood applications. Therefore, a second system that is only used for nonfood systems could be an easy way to screen and select for food or nonfood maize.

6) Use of non germinating seeds: This would entail that seeds derived from production fields would not germinate on their own without a specific treatment eliminating plants growing in unexpected areas for any reason.

In a preferred system, all of these characteristics may be employed together but adding any one of the genetic safety features could increase the safety margin and reduce concerns of inadvertent mixing. We are unaware of any crop today that can provide this full set of characteristics for enhanced product and environmental safety. However, with the exception of a non-germinating seed, all of the above attributes are already available in maize germplasm.

Example—Preparation of Gene Constructs

Figure 2:
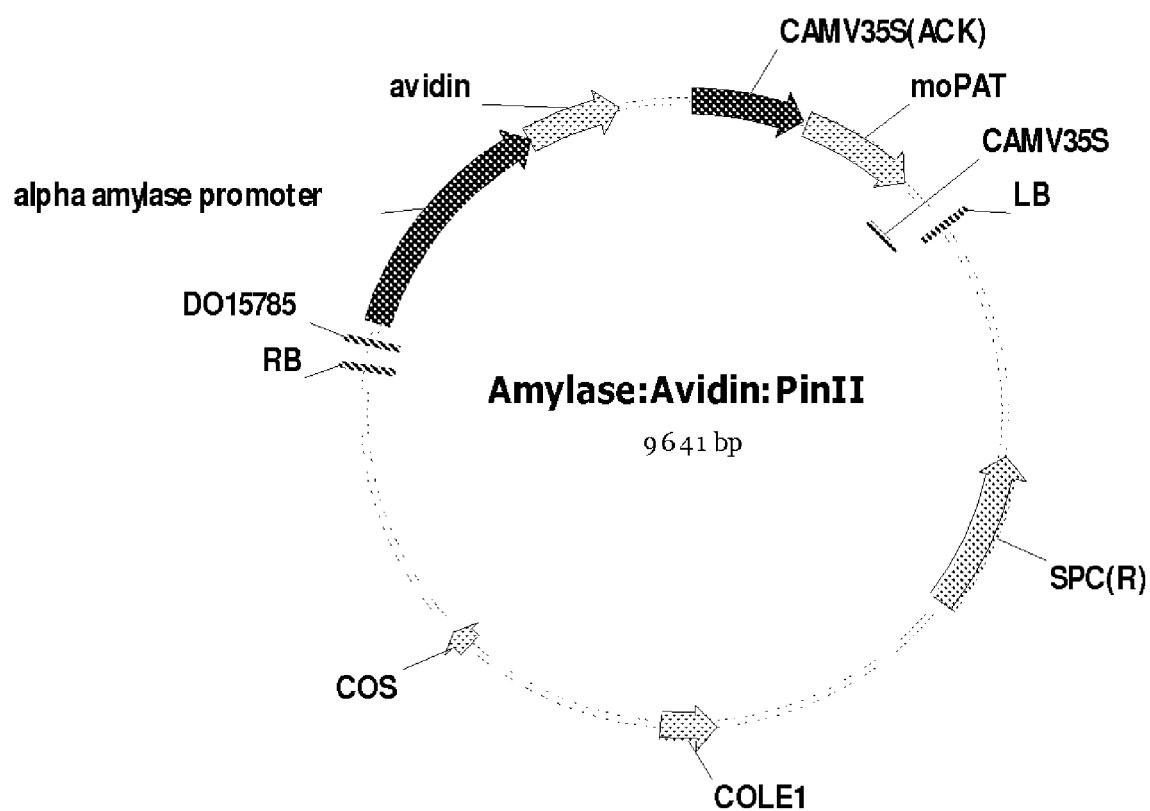
FIG. 2 is a graphic representation of a construct containing an alpha amylase promoter driving avidin and other sequences used for plant transformation.

One construct to be used would target avidin to the cytoplasm driven by a barley alpha amylase promoter. This would be linked to a selectable marker cassette consisting of the PAT gene driven by the 35S promoter and incorporating the 35S termination sequence (FIG. 2). A similar construct would replace the avidin gene with a gene for beta-glucuronidase in order to monitor the expression of the promoter.

Figure 3:
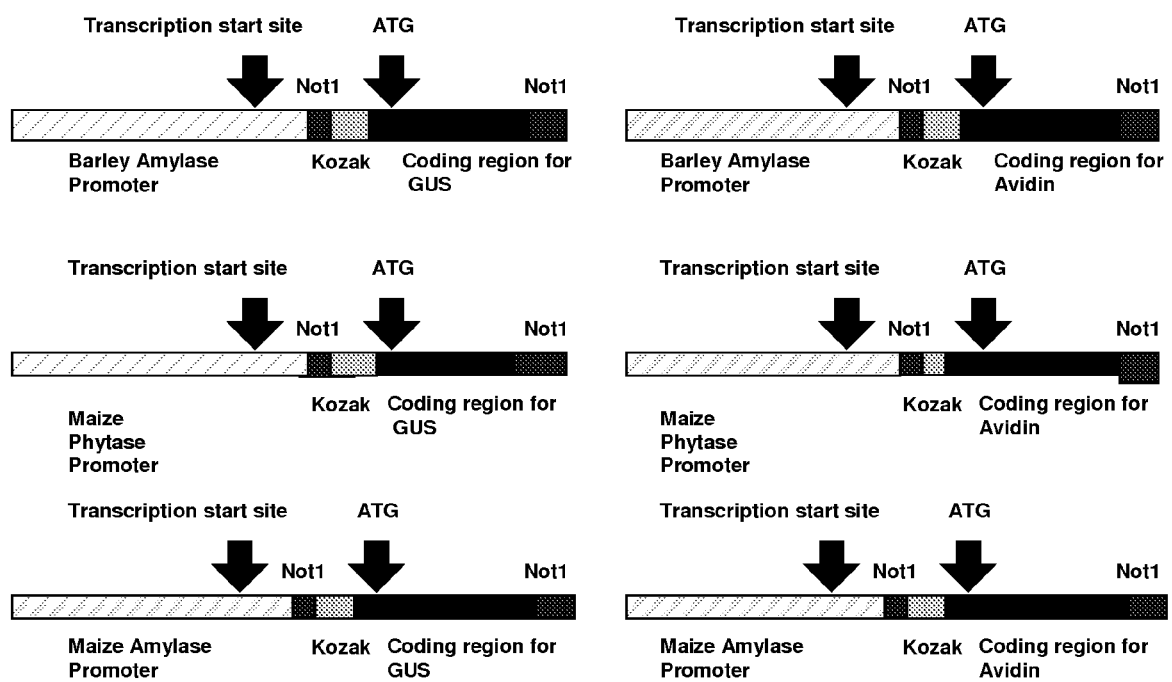
FIG. 3: is a graphic representation of constructs made with three different germination preferred promoters expressing either GUS or avidin.

Both constructs were successfully made and introduced in *Agrobacterium* to be used in plant transformation experiments. Other maize germination preferred promoters are expected to be preferred for use in corn tissue as discussed supra. This includes the maize amylase promoter and the maize phytase promoter (24, 25). We have successfully cloned both of these additional promoters to drive expression of either the avidin or GUS genes. FIG. 3 list the constructs made.

Example—Demonstrate Germination/Growth Inhibition

Figure 4:
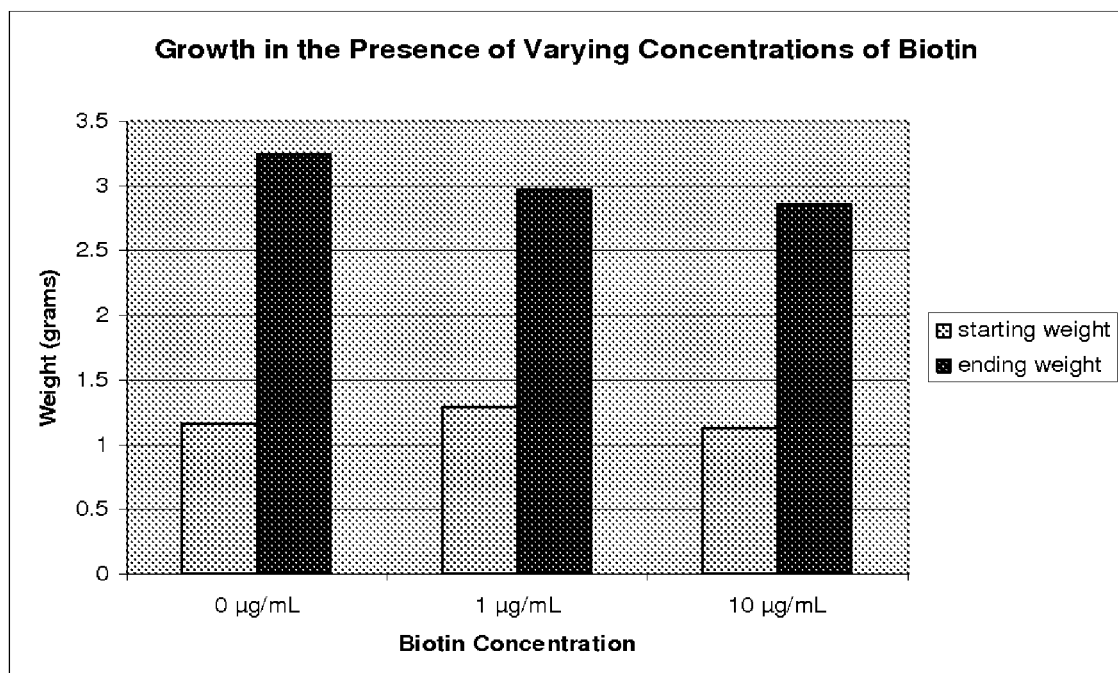
FIG. 4 is a graph showing growth of transformed cell cultures with and without biotin.

We transformed the avidin gene driven by the barley promoter into *Agrobacterium*, followed by transformation into plants. Avidin expression should only occur during germination and therefore present no growth inhibition in the remainder of the plant cycle. While the amylase promoter has been shown to be highly specific in barley plants, we have conducted tests to determine if specificity of expression is maintained in corn tissue or if the promoter can drive expression in cell culture. Therefore, for routine transformations with avidin constructs, we added biotin in the culture media to counteract any effects of avidin as a precaution. Unlike our previous attempts to express avidin in the cytoplasm using a constitutive promoter, we saw no effects of the avidin gene on transformation and were able to obtain over 20 transformation events using herbicide selection. To test for potential inhibition of growth by avidin due to leaky expression of the promoter, selected transformed cell cultures were grown either in the presence or absence of biotin. FIG. 4 shows that there was no significant difference in growth of cultures with or without biotin in the media suggesting that the promoter does not express in cell cultures. Multiple lines were transferred every two weeks over a period of six weeks. The graph of FIG. 4 represents a typical result in that no significant difference in growth could be seen with or without biotin in the media.

To confirm the specificity of this promoter, we tested transformed cell lines with the beta-glucuronidase (GUS) gene and evaluated GUS staining as an indicator of expression (25). Embryos were transformed with the GUS gene and examined after one week for GUS activity. Occasionally we could see only a single cell staining. This was in stark contrast to the constitutively expressed GUS gene using the ubiquitin promoter that showed ample expression of darkly stained clusters of cells in the transient assay. In addition to these transient assays, stable cultures selected on herbicide resistance were also tested but there was no evidence of any GUS activity. This supports the earlier avidin results and suggests that the promoter has little or no expression in cell cultures Example—Demonstrate Seed Sterility and Reversal with Biotin in a Germination Preferred Manner Initially non-transformed seeds were tested at several concentrations of biotin to ensure that biotin had no effect. Seeds tolerated up to 10 μg/ml of biotin in water used for imbibing the seeds with no detrimental signs of any effect on germination. Seeds from the first transformation events containing the avidin gene were then tested for germination with and without biotin in the water. Since our $T_0$ plants were crossed with non-transgenic maize in the greenhouse, it is expected that half of the seeds in our initial transformed plants ($T_1$ seed) should not carry the avidin gene. If avidin is fully effective in preventing germination in transgenic seed, we would predict an overall close to about 50% germination rate without biotin. In addition, if the system is working as expected, we would expect close to about 100% of seeds to germinate with biotin.

Figure 5:
FIG. 5 shows PCR results from maize seedlings; the top row represents plants germinated in water, and in the bottom row germination on biotin.
Figure 5:

The best results obtained showed after one week seeds without biotin had a lower germination rate than the biotin treated seeds, suggesting inhibition by avidin. In this case, 40 seeds were taken from a single ear of transformed corn and 20 seeds were imbibed with and 20 seeds without biotin. 7 seeds out of 20 failed to germinate without biotin (FIG. 5—upper) whereas in the case of biotin treatment only one seed failed to germinate (FIG. 5—lower). This is very close to what we would have predicted. The one seed that did not germinate on biotin treatment could be caused by not having enough biotin or simply a non-germinating seed. Our greenhouse seed typically shows a 95% germination rate and we would expect a small number not to germinate under any circumstance. The effectiveness varied with different tests from this best case shown above to some tests that showed no inhibition at all. Over several experiments testing 240 seeds, 20% of seed tested did not germinate on water as opposed to the predicted 50%. The number of non germinating seeds was cut in half when biotin was applied during imbibing. A range of expression is to be expected in early transgenic plants, and, as the results above show, avidin is functional in the system at various levels of expression. We normally observe variation in transgene protein expression (particularly in $T_1$ seed) among events as well as between plants within an event which may account for our variation in results. To test whether expression of avidin may allow the seeds to germinate but fail to mature or grow at a slower rate we examined the growth of seedlings immediately following germination. The results in Table 1 are representative of what we have seen for several different experiments. In this case, the vast majority of transgenic seedlings grew faster with biotin than without. These growth results reflect the expected results in that approximately half of the seeds are not expected to show any difference in growth rate on biotin while the remainder should be inhibited and only restored in the presence of biotin.

TABLE 1

Representative relative growth rates of plants with and without biotin
Seeds were rated for growth 3 days after treatment with or without biotin. The number of plants in each category was measured as: no growth; slow growth-root length < 1 cm; rapid growth-root length >= 1 cm

| Rating | Without Biotin | With Biotin |
|---|---|---|
| No growth | 9 | 2 |
| Slow growth | 4 | 3 |
| Rapid growth | 7 | 15 |

Example—Characterize the Efficiency of this System

To diagnose the effectiveness of the barley promoter, we examined the $T_1$ seeds with the GUS construct. GUS staining was applied 0, 1, 2, 3 or 4 days after imbibing the seeds. The low level of stain with the barley alpha amylase was compared with that when the ubiquitin promoter is used using the following combinations: Ubiquitin-GUS seed 3 days after imbibition (d.a.i.); amylase-GUS seed 0 d.a.i.; amylase-GUS seed 1 d.a.i.; amylase-GUS seed 2 d.a.i.; amylase-GUS seed 3 d.a.i.; and amylase-GUS seed 4 d.a.i. The expression of GUS is absent at day 0 and is maximum at days 1-3 when the barley amylase promoter is used. This is what we had hoped for with regard to germination expression specificity. Even thought the level of expression of GUS at its peak with the barley amylase promoter is a fraction of that using the ubiquitin promoter, it still is functional. In addition, alternative constructs using maize germination preferred promoters as described earlier (FIG. 3). In the case of the phytase promoter, we have also prepared constructs with two versions of the promoter, one of which includes an intron located in the 5' untranslated region of the promoter and one without this intron (See FIG. 7 for the promoter with the intron (SEQ ID NO: 2) and without the intron (SEQ ID NO: 3)—the intron is in italics and the ATG start site underlined and bold). The addition of an intron upstream of the translation start site is often used to enhance expression levels in corn. We have selected over 30 transformation events for constructs using the phytase promoter and these are in the process of being regenerated into plants which will subsequently be grown to maturity and the seed collected. We have also initiated plant transformation experiments with the maize amylase promoter in order to test for sufficient specificity of the promoter. Advantages of seed expression will be explored by use of the maize promoters described below, along with making alternative intracellular targeting sites.

Example: Obtain Seeds of Transformed Plants with New Alternative Constructs

Either the maize phytase or the amylase promoter are anticipated to result in increased expression of avidin and decreased seed germination. Additional constructs will be made to further improve the system. We have described several constructs to be made below.

In one experiment the constructs include a maize alpha amylase promoter discovered by the inventors. A putative promoter sequence adjacent to the coding region for the Amy3 gene (GenBank L25805) from a newly available maize BAC clone was sequenced. The sequence is shown in FIG. 6 (SEQ ID NO: 1).

By making these in phases we can evaluate the previous results to select the most appropriate characteristics for the next set of constructs. These are discussed below and summarized in Table 2. The analysis of the constructs is described below.

TABLE 2

Proposed constructs
The constructs of the preceding phase will be used to determine the characteristics of the following constructs. BAA = barley alpha amylase; MP = maize phytase; MAA = maize alpha amylase.

| Gene | Target | Promoter |
|---|---|---|
| Avidin | Cyto | BAA |
| GUS | Cyto | BAA |
| Avidin | Cyto | MP |
| GUS | Cyto | MP |
| Avidin | Cyto | MAA |
| GUS | Cyto | MAA |

Another version is the barley amylase promoter that also has an intron from the same gene added in the leader sequence just upstream of the transcription start site Lead constructs were made with the barley promoter. Maize promoters targeted to the cytoplasm are also used. Expression may be higher using the maize germination preferred promoters described earlier. These constructs (FIG. 3) have already been made and the strength of and specificity of the promoter can be verified using the GUS gene independent of the effects of avidin expression. The avidin constructs will also be analyzed as described below. When analyzing these various constructs, we are left with a mixed population of seed with respect to the avidin gene and variation in expression between plants that can complicate our results. While PCR or herbicide resistance can assess for the presence of the gene, this does not address the level of expression. Normally, we would measure the expression of the foreign protein directly in $T_1$ seed to select the best lines to advance. Plants are then selected at subsequent generations for high expressing stable lines and become much more uniform in expression. In our case however, high expression of avidin will kill the cells so we cannot use this approach, making it more difficult to analyze these early constructs.

Example—Test the Efficacy of the Different Constructs

Seeds from these individual plants will be analyzed as follows:

A. GUS constructs will be stained for activity to determine relative promoter strength in the early stages of germination, day 0, 1, 2, 3 and 4. Sixty seeds will be taken from individual ears and 10 seeds will be used for each time point. Ten seedlings will be grown to maturity to test selected mature tissues for GUS activity to confirm the expected specificity of promoter activity. If we cannot differentiate easily by staining tissue, we will use the quantitative GUS assay described previously (31).

B. All constructs containing avidin will be tested for inhibition of germination and reversal with biotin. 40 seeds from individual ears will be imbibed with and without biotin and the germination rate will be observed over a one week period.

C. Plants germinating in the presence or absence of biotin will be tested for herbicide resistance by leaf painting to determine which individual plants contain the gene.

D. Plants germinating in the absence of biotin will be subjected to PCR analysis to confirm the presence or absence of the gene. This will be correlated with leaf painting for herbicide resistance.

E. In the event we obtain plants that germinate in the absence of biotin and show the presence of the avidin gene, we will also examine the possibility of assaying avidin directly as described previously (31). This will be done only at a time where the GUS staining of the promoter indicates expression is likely.

Information from this analysis will allow us to determine 1) the relative strength of the promoter, 2) the relative effectiveness of the different constructs to inhibit germination, and 3) the ability of biotin to reverse the inhibition. The herbicide resistance, PCR analysis and avidin assay will be used to differentiate which plants at the $T_1$ stage are escapes in that that they contain the avidin gene but can still germinate rather than plants that are escapes in that they do not contain any transgenic genes. This information will then be used to select the most promising constructs.

BIBLIOGRAPHY AND REFERENCES CITED

1. Hood, E. E. and J. A. Howard (eds.) *Plants as Factories for Protein Production*. Kluwer Academic Publishers, Dordrecht, The Netherlands (2002).
2. USDA; information regarding conditions placed on the introduction of plants engineered for production of pharmaceuticals and industrial, beginning with the 2003 growing season, is found in Mar. 10, 2003 Federal Register Notice at: worldwide web at aphis.usda.gov. See also User's Guide for Release Permits at: would wide web at aphis.usda.gove/brs/pdf/usersguide.pdf.
3. American Coalition for Ethanol at: world wide web ethanol.org.
4. Corn Annual 2001, Corn Refiners Association, at: world wide web at corn.org/web/ca2001.htm.
5. Nikolov, Z. L., J. B. McClellan and E. E. Hood. Production of therapeutic proteins from transgenic maize. Pharmaceutical Visions: 28-30 (Autumn 2002).
6. Streatfield, S. J., J. R. Lane, C. A. Brooks, D. K. Barker, M. L. Poage, J. M. Mayor, B. J. Lamphear, C. F. Drees, J. M. Jilka, E. E. Hood and J. A. Howard. Corn as a production system for human and animal vaccines. Vaccine 21:812-815 (2003).
7. Howard, J. A and E. E. Hood. Bioindustrial and biopharmaceutical products produced in plants. Advances in Agronomy 85: 91-123 (2005).
8. ProdiGene at: world wide web at prodigene.com/index.htm
9. Hood, E., R. Love, J. Lane, J. Bray, R. Clough, K. Pappu, C. Drees, K. Hood, S. Yoon, A. Ahmad, and J. Howard. Subcellular targeting is a key condition for high-level accumulation of cellulase protein in transgenic maize seed. Plant Biotechnology Journal 5(6): 709-719 (2007).
10. J. A. Howard and E. E. Hood Methods for Growing Nonfood Products in Transgenic Plants. Crop Science 47:1255-1262 (2007).
11. Hood, E. E., J. A. Howard and D. Delaney. Methods of increasing expression of heterologous proteins in plants. US Patent Application Number US20020782078, published Oct. 10, 2004.
12. Moose, S. P., J. W. Dudley and T. R. Rocheford. Maize selection passes the century mark: a unique resource for $21^{st}$ century genomics. Trends in Plant Science 9:358-364 (2004).
13. Maize Genetics and Genomics Database, red kernel (phenotype) at: world wide web at maizegdb.org/cgi-bin/displayphenorecord.cgi?id=56383, orange kernel (phenotype) at: world wide web at maizegdb.org/cgi-bin/displayphenorecord.cgi?id=56384, blue kernel (phenotype) at: world wide web at maizegdb.org/cgi-bin/displayphenorecord.cgi?id=65525, black kernel (phenotype) at: world wide web at maizegdb.org/cgi-in/displayphenorecord.cgi?id=63932.
14. Levings, C. S. III. Thoughts on cytoplasmic male sterility in cms-T maize. The Plant Cell 5:1285-1290 (1993).
15. Albertsen, M. C., J. A. Howard and S. Maddock. Induction of male sterility in plants by expression of high levels of avidin. U.S. Pat. No. 5,962,769, Oct. 5, 1999.
16. Dumas, R. The intracellular localization of holocarboxylase synthetase. Graduate Thesis, Department of Biology, McGill University, Montreal, Canada, 1999.
17. Hood, E. E., D. R. Witcher, S. Maddock, T. Meyer, C. Baszczynski, M. Bailey, P. Flynn, J. Register, L. Marshall, D. Bond, E. Kulisek, A. Kusnadi, R. Evangelista, Z. Nikolov, C. Wooge, R. I. Mehigh, R. Hernan, W. K. Kappel, D. Ritland, C. P. Li and J. A. Howard. Commercial production of avidin from transgenic maize: characterization of transformant, production, processing, extraction and purification. Molecular Breeding 3: 291-306 (1997).
18. Khursheed B. and J. C. Rogers. Barley α-amylase genes: quantitative comparison of steady-state mRNA levels from individual members of the two different families expressed in aleurone cells. Journal of Biological.Chemistry 263 (35):18953-18960 (1988).
19. Jensen, L. G., O. Olsen, O. Kops, N. Wolf, K. K. Thomsen and D. von Wettstein. Transgenic barley expressing a protein-engineered, thermostable (1,3-1,4)-β-glucanase during germination. Proceedings of the National Academy of Sciences USA 93: 3487-3491 (April 1996).
20. Nuutila A. M., A. Ritala, R. W. Skadsen, L. Mannonen and V. Kauppinen. Expression of fungal thermotolerant endo-1,4-β-glucanase in transgenic barley seeds during germination. Plant Molecular Biology 41: 777-783 (1999).
21. Grosset, J., R. Alary, M-F Gautier, M. Menossi, J. A. Martinez-Izquierdo and P. Joudrier. Characterization of a barley gene coding for an α-amylase inhibitor subunit (CMd protein) and analysis of its promoter in transgenic tobacco plants and in maize kernels by microprojectile bombardment. Plant Molecular Biology 34: 331-338 (1997).
22. Gallie, D. R. and T. E. Young. The regulation of gene expression in transformed maize aleurone and endosperm protoplasts. Analysis of promoter activity, intron enhancement, and mRNA untranslated regions on expression. Plant Physiol. 106: 929-939 (1994).
23. Young, T. E., D. A. DeMason and T. J. Close. Cloning of an α-amylase cDNA from aleurone tissue of germinating maize seed. Plant Physiology 105:759-760 (1994).
24. Maugenest, S., I. Martinez and A. Lescure. Cloning and characterization of a cDNA encoding maize seedling phytase. Biochemical Journal (1997) 322:511-517.
25. Maugenest, S., I. Martinez, B. Godin, P. Perez and A. Lescure. Structure of two maize phytase genes and their spatio-temporal expression during seedling development. Plant Molecular Biology 39:503-514 (1999).
26. Virginia Cooperative Extension. Terminator technology for transgenic crops. http://filebox.vt.edu/users/chagedor/fileboxmigration/cals/cses/chagedor/terminator.html.
27. Oliver, M. J., J. E. Edwin, N. L. G. Trolinder, D. L. Keim. Control of plant gene expression (Terminator gene control). U.S. Pat. No. 5,723,765, Mar. 3, 1998.
28. Beauregard, M. and M. A. Hefford. Enhancement of essential amino acid contents in crops by genetic engineering and protein design. Plant Biotechnology Journal 4 (5): 561-574 (2006).
29. Hood E. E., M. R. Bailey, K. Beifuss, M. E. Horn, M. Magallanes-Lundback, C. Drees, D. Delaney, R. Clough, J. A. Howard. Criteria for high-level expression of a fungal laccase gene in transgenic maize. Plant Biotechnology Journal 1:129-140 (2003).
30. N. C. A. de Ruijter, J. Verhees, W. van Leeuwen, A. R. van der Krol. Evaluation and comparison of the GUS, LUC and GFP reporter system for gene expression studies in plants. Plant Biol (Stuttg) 5: 103-115 (2003).

31. Streatfield, S., M. Magallanes-Lundback, K. Beifuss, C. Brooks, R. Harkey, R. Love, J. Bray, J. Howard, J. Jilka and E. Hood. Analysis of the maize polyubiquitin-1 promoter heat shock elements and generation of promoter variants with modified expression characteristics. Transgenic Research 13: 299-312 (2004).

What is claimed is:

1. A method of controlling germination of a plant seed, the method comprising:

introducing into a plant cell a nucleic acid molecule encoding an avidin or streptavidin protein wherein said avidin or streptavidin protein inhibits germination of said plant seed when not exposed to a restoring compound of biotin and said avidin or streptavidin protein will not inhibit germination when exposed to said biotin restoring compound, said nucleic acid molecule operably linked to a promoter which expresses said avidin or streptavidin protein during germination of said plant seed, and producing plant seed comprising said nucleic acid molecule, such that germination of said plant seed is controllable.

2. The method of claim 1, wherein said plant seed comprising said nucleic acid molecule is not exposed to said restoring compound and germination of said seed is inhibited.

3. The method of claim 1, wherein said plant seed comprising said nucleic acid molecule is exposed to said restoring compound and germination of said seed is not inhibited.

4. The method of claim 1, wherein said promoter directs expression of said protein at higher levels during seed germination than when seed germination is not occurring.

5. The method of claim 4, wherein said protein prevents plant cell formation, function or growth, and said promoter directs expression at levels when seed germination is not occurring such that plant cell formation, function or growth is not prevented.

6. The method of claim 1, wherein said promoter is selected from the group consisting of an alpha amylase promoter and a phytase promoter.

7. The method of claim 1, wherein said promoter is selected from the group consisting of SEQ ID NO: 1 or fragments thereof which express an operably linked protein in a germination-preferred manner.

8. A method of controlling germination of a plant seed, the method comprising:

introducing into a plant seed a nucleic acid molecule encoding avidin, streptavidin or other biotin binding protein, said nucleic acid molecule operably linked to a promoter which expresses said avidin streptavidin or other biotin binding protein during germination of said plant seed, producing plant seed comprising said nucleic acid molecule, and controlling germination by a method selected from the group consisting of: preventing exposure of said seed to biotin and inhibiting germination, and exposing said plant seed to biotin and allowing germination of said seed.

9. The method of claim 8 wherein said promoter is selected from the group consisting of alpha amylase and phytase promoters.

10. The method of claim 8, wherein said plant seed is exposed to biotin such that plant seed germination is not inhibited.

11. The method of claim 8, wherein said promoter is selected from the group consisting of SEQ ID NO: 1 or fragments thereof which express an operably linked protein in a germination-preferred manner.

12. A plant seed having controllable germination comprising: a heterologous nucleic acid molecule encoding an avidin, streptavidin or other biotin binding protein wherein said protein inhibits germination of said plant seed when not exposed to a biotin restoring compound and said protein will not inhibit germination when exposed to said restoring compound, said nucleic acid molecule operably linked to a promoter which expresses said protein during germination of said plant seed, and producing plant seed comprising said nucleic acid molecule, such that germination of said plant seed is controllable.

13. The plant cell of claim 12, wherein said protein is selected from the group consisting of avidin and streptavidin.

14. The plant cell of claim 13, wherein said promoter is selected from the group consisting of an alpha amylase promoter and a phytase promoter.

15. The plant cell of claim 13, wherein said promoter is selected from the group consisting of SEQ ID NO: 1 or fragments thereof which express an operably linked protein in a germination-preferred manner.

16. A method regulating expression of a nucleic acid molecule comprising operably linking said nucleic acid molecule with a regulatory region selected from the group consisting of SEQ ID NO: 1 or functional fragments thereof which express an operably linked protein in a germination-preferred manner.

17. A plant cell comprising a heterologous regulatory region from the group consisting of SEQ ID NO: 1 or functional fragments thereof which express an operably linked protein in a germination-preferred manner.

* * * * *